US012698345B2

(12) United States Patent
Bhavsar et al.

(10) Patent No.: US 12,698,345 B2
(45) Date of Patent: Aug. 4, 2026

(54) PROCESS FOR IMPROVING OMALIZUMAB EXPRESSION IN CHO CELLS

(71) Applicant: Kashiv BioSciences, LLC, Piscataway, NJ (US)

(72) Inventors: Kaumil Bhupendra Bhai Bhavsar, Ahmedabad (IN); Ghanshyam Madhabhai Patel, Gandhinagar (IN); Parth Hitarthbhai Vaishnav, Jamnagar (IN)

(73) Assignee: Kashiv BioSciences, LLC, Piscataway, NJ (US)

( * ) Notice: Subject to any disclaimer, the term of this patent is extended or adjusted under 35 U.S.C. 154(b) by 0 days.

(21) Appl. No.: 18/429,203

(22) Filed: Jan. 31, 2024

(65) Prior Publication Data
US 2024/0287207 A1 Aug. 29, 2024

Related U.S. Application Data

(63) Continuation of application No. PCT/IB2023/051765, filed on Feb. 25, 2023.

(30) Foreign Application Priority Data

Feb. 25, 2022 (IN) ............................. 202221010310

(51) Int. Cl.
*C07K 16/42* (2006.01)

(52) U.S. Cl.
CPC ...... *C07K 16/4291* (2013.01); *C07K 2317/14* (2013.01); *C07K 2317/41* (2013.01)

(58) Field of Classification Search
None
See application file for complete search history.

(56) References Cited

U.S. PATENT DOCUMENTS

| | | | |
|---|---|---|---|
| 6,172,213 B1 * | 1/2001 | Lowman | A61P 37/00 |
| | | | 435/69.6 |
| 2013/0344084 A1 | 12/2013 | Subramanian et al. | |
| 2014/0274912 A1 | 9/2014 | Prentice | |
| 2017/0107553 A1 | 4/2017 | Kottakota et al. | |
| 2017/0166941 A1 | 6/2017 | Jung et al. | |
| 2019/0153497 A1 | 5/2019 | Jordan et al. | |
| 2020/0172947 A1 | 6/2020 | Leiske et al. | |

OTHER PUBLICATIONS

Mchugh et al., Biotechnol Prog. May 2020;36(3):e2959. doi: 10.1002/btpr.2959. Epub Jan. 17, 2020. PMID: 31930722.*
Kunert et al., Appl Microbiol Biotechnol. Apr. 2016;100(8):3451-61. doi: 10.1007/s00253-016-7388-9. Epub Mar. 3, 2016. PMID: 26936774.*
Hogiri et al., J Biosci Bioeng. Feb. 2018;125(2):245-250. doi: 10.1016/j.jbiosc.2017.08.015. Epub Sep. 28, 2017. PMID: 28964661.*
Presta et al., J Immunol. Sep. 1, 1993;151(5):2623-32. PMID: 8360482.*
Hodoniczky et al. (2005) "Control of Recombinant Monoclonal Antibody Effector Functions by Fc N-Glycan Remodeling in Vitro," Biotechnol. 21:1644-1652.
Szabo et al. (2022) "N-glycosylation structure—function characterization of omalizumab, an anti-asthma biotherapeutic product," Journal of Pharmaceutical and Biomedical Analysis 209:114483 5 pages.
International Search Report dated Jul. 7, 2023 issued in International Application No. PCT/IB2023/051765.
Ayyar et al., "Optimizing antibody expression: The nuts and bolts", Methods, vol. 116, Mar. 1, 2017, pp. 51-62; DOI: 10.1016/j.ymethy.2017.01.009.

* cited by examiner

*Primary Examiner* — Michael Szperka
(74) *Attorney, Agent, or Firm* — Goodwin Procter LLP

(57) ABSTRACT
The present invention relates to a process of improving the production of anti-IgE antibody specifically Omalizumab with improved titer and reduced galactosylation and/or reduced acidic variant expressed in mammalian cell culture in suitable culture condition for an example using fed batch mode by maintaining specific temperature 36.5° C.±0.5 throughout the duration of cells culture.

12 Claims, No Drawings

PROCESS FOR IMPROVING OMALIZUMAB EXPRESSION IN CHO CELLS

CROSS-REFERENCE TO RELATED APPLICATIONS

This application is a Continuation of International Patent Application No. PCT/IB2023/051765, filed on Feb. 25, 2023, which claims the benefit of Indian Patent Application number 202221010310, filed on Feb. 25, 2022, the contents of each of which are hereby incorporated by reference in their entirety.

FIELD OF INVENTION

The present invention relates to a process for improving the production of anti-IgE antibody specifically Omalizumab with improved titer and reduced galactosylation and/or reduced acidic variant expressed in mammalian cells culture in suitable culture condition for an example using fed batch mode by maintaining specific temperature 36.5° C.±0.5 throughout the duration of cell culture.

BACKGROUND

Mammalian cell cultures such as Chinese hamster ovary (CHO) cells are widely used for the commercial production of therapeutic biomolecules like monoclonal antibodies and proteins. Several process parameters like pH, temperature, pO2, CO2, air flow, feeding, agitation rate etc. are essential to maintain cells in a culture environment. Temperature and pH being one of the critical parameters requires optimization for enhanced cell growth, viability, productivity for the generation of therapeutic biomolecules. The optimization of fed batch culture for the production of monoclonal antibodies with desired quantity with desired quality is a challenging process and usually it depends on particular biotherapeutic molecule as well. The present invention provides an optimized temperature 36.5° C.±0.5 during cell culture and maintains suitable pH below 7 during production phase to express desired titer and maintains desired characteristics like reduced galactosylation and/or reduced acidic variant of antibody. The present disclosure provides an optimized temperature 36.5° C.±0.5 during fed batch process and maintains suitable pH between about 6.7 to about 6.9 during production phase of fed batch process for the production of desired titer with suitable characteristics reduced galactosylation and/or reduced acidic variant of antibody.

SUMMARY OF INVENTION

The present invention provides a cell culture process for the production of omalizumab expressed in mammalian cells culture in fed batch mode by maintaining specific temperature 36.5° C.±0.5 throughout the cell culture wherein the fed batch process produces the desired titer of omalizumab with reduced galactosylation and/or reduced acidic variant compared to cell culture process performed at temperature other than 36.5° C.±0.5.

The present invention provides a cell culture process for the production of omalizumab expressed in mammalian cells culture in fed batch mode by maintaining specific temperature 36.5° C.±0.5 throughout the cell culture and maintain suitable pH below 7 during production phase wherein the fed batch process produces the desired titer of omalizumab with reduced galactosylation and/or reduced acidic variant compared to cell culture process performed at temperature other than 36.5° C.±0.5 and pH at or above 7.

The present invention provides a process for the production of antibody of interest expressed in mammalian cells culture medium in fed batch mode by maintaining specific temperature 36.5° C.±0.5 throughout the cell culture and at least pH below 7 during the production phase wherein the fed batch process provides the antibody of interest in high titer with reduced galactosylation and/or reduced acidic variant compared to production phase performed at 37.5° C. and pH 6.7.

In an embodiment, the cell culture process for producing anti-IgE antibody in mammalian cell culture is performed at 36.5° C. to obtain desired product profile selected from high titer and improved characteristics selected from reduced galactosylation and reduced acidic charge variants.

In an embodiment, a process for improving the expression of anti-IgE antibody in mammalian cell culture comprising;
 a) culturing the mammalian cell capable to express an anti-IgE antibody in the mammalian cell culture;
 b) maintaining suitable temperature at 36.5° C.±0.5° C. throughout the mammalian cell culture;
 c) harvesting the anti-IgE antibody from mammalian cell culture;
 wherein the process improves the titer and has at least 50% high titer and the characteristics of anti-IgE antibody selected from reduced galactosylation and reduced acidic variants.

In an embodiment, the suitable temperature is about 36° C. to about 36.5° C.

In an embodiment, a process for improving the expression of anti-IgE antibody in mammalian cell culture comprising;
 a) culturing the mammalian cell capable to express an anti-IgE antibody in the mammalian cell culture;
 b) maintaining suitable temperature at 36.5° C. throughout the mammalian cell culture;
 c) harvesting the anti-IgE antibody from mammalian cell culture;
 wherein the process improves the titer and characteristics of anti-IgE antibody selected from reduced galactosylation and reduced acidic variants.

In an embodiment, the suitable temperature is 36.5±0.5° C.

In an embodiment, a process for improving the expression of omalizumab in mammalian cell culture comprising;
 a) culturing the mammalian cell capable to express omalizumab in the mammalian cell culture;
 b) maintaining suitable temperature 36.5° C.±0.5 throughout the mammalian cell culture;
 c) maintaining about pH 6.8±0.1 during the production phase of mammalian cell culture;
 d) harvesting omalizumab from mammalian cell culture;
 wherein the process improves the titer and characteristics of omalizumab selected from reduced galactosylation and reduced acidic variants.

In an embodiment, the suitable pH less than 7 maintained during the production phase.

In an embodiment, the suitable pH selected from about pH 6.7, about pH 6.8, and about 6.9.

In an embodiment, the suitable pH is maintained during the production phase on day selected from Day 3, Day 4, Day 5, Day 6, Day 7, Day 8, Day 9, Day 10, Day 11, and Day 12.

In an embodiment, a process for the production of antibody comprising:
 a) culturing the mammalian cell capable to express antibody of interest in the bioreactor;

b) maintaining the suitable temperature 36.5° C. throughout the cell culture and at least pH about 6.8 during the production phase in the bioreactor;

c) harvesting the antibody of interest from bioreactor comprising mammalian cell culture;

wherein the antibody of interest has at least 50% high titer compared to the mammalian cell is cultured during production phase at above 36.5° C. and pH less than 6.8.

In an embodiment, a process for the production of antibody comprising:

a) culturing the mammalian cells capable to express antibody of interest in the bioreactor;

b) maintaining the suitable temperature 36.5° C. throughout the cell culture and at least pH about 6.8 during the production phase in the bioreactor;

c) harvesting the antibody of interest from mammalian cell culture in the bioreactor;

wherein the antibody of interest has at least 50% high titer and reduced galactosylation compared to the mammalian cell is cultured during production phase at above 36.5° C. and pH less than 6.8.

In an embodiment, a process for the production of omalizumab comprising:

a) culturing the mammalian cell capable to express omalizumab in the bioreactor;

b) maintaining the suitable temperature 36.5° C. throughout the cell culture and at least pH about 6.8 during the production phase in the bioreactor;

c) harvesting omalizumab from mammalian cell culture contains at least 50% high titer and reduced galactosylation and/or reduced acidic variants compared to the mammalian cell is cultured during production phase at above 36.5° C. and pH less than 6.8.

In an embodiment, a process for the production of antibody comprising:

a) culturing the mammalian cell capable to express antibody of interest in the bioreactor;

b) maintaining the mammalian cell at one suitable temperature set point and at first pH in the bioreactor;

c) maintaining the mammalian cell at one suitable temperature set point and at second pH in the bioreactor wherein the second pH is at least one log lower than first pH;

d) harvesting the antibody of interest from mammalian cell culture in the bioreactor;

wherein the antibody of interest has reduced galactosylation and/or reduced acidic variants.

In certain embodiment the pH is maintained below 7 during production phase.

In certain embodiment the cell culture process is initiated at or above pH 7 preferably pH 7.1 or pH7.2 and reduced to pH below 7 preferably pH 6.7 to 6.9.

In certain embodiment, the second pH is lower than first pH by unit selected from one log, two log, three log.

In certain embodiment, the first pH is selected from pH 6.8, 6.9, 7.0.

In certain embodiment, the first pH is maintained for suitable period selected from Day 0, Day 1, Day 2 and Day 3.

In certain embodiment, the second pH is selected from pH 6.5, 6.6, 6.7 6.8, 6.9, 7.0, 7.1 and 7.2.

In certain embodiment, the second pH is maintained for suitable period selected from Day 4, Day 5, Day 6 and Day 7, Day 8, Day 9, Day 10, Day 11 and Day 12.

DETAILED DESCRIPTION OF THE INVENTION

The present invention relates to a process of improving polypeptide expression in mammalian cells culture in fed batch mode by maintaining specific temperature throughout the cell culture process & suitable pH throughout the production phase of the cell culture.

The present invention relates to a cell culture process for producing anti-IgE antibody in mammalian cell culture performed at 36.5° C. to obtain desired product profile selected from high titer, reduced galactosylation and reduced acidic charge variants.

The present invention provides a cell culture process for the production of omalizumab expressed in mammalian cells culture in fed batch mode by maintaining specific temperature 36.5° C.±0.5 throughout the cell culture wherein the fed batch process produces the omalizumab with reduced galactosylation and/or reduced acidic variant compared to cell culture process performed at temperature other than 36.5° C.±0.5.

The present invention provides a cell culture process for the production of omalizumab expressed in mammalian cells culture in fed batch mode by maintaining specific temperature 36.5° C.±0.5 throughout the cell culture and maintain suitable pH below 7 during production phase wherein the fed batch process produces the omalizumab with reduced galactosylation and/or reduced acidic variant compared to cell culture process performed at temperature other than 36.5° C.±0.5 and pH at or above 7.

The present invention provides a process for the production of omalizumab expressed in mammalian cells culture in fed batch mode by maintaining specific temperature 36.5° C.±0.5 throughout cell culture wherein the fed batch process provides omalizumab with reduced galactosylation and/or reduced acidic variant compared to fed batch process performed at 37.5° C.

The present invention provides a process for the production of antibody of interest expressed in mammalian cells culture in fed batch mode by maintaining specific temperature 36.5° C.±0.5 throughout cell culture and at least pH below 7 during the production phase wherein the fed batch process provides the antibody of interest with reduced galactosylation and/or reduced acidic variant compared to fed batch process performed at 37.5° C. and pH 6.7.

The present invention relates to a process of improving omalizumab biosimilar expression in mammalian cells culture in fed batch mode by maintaining specific temperature 36.5° C.±0.5 throughout the culturing duration.

The present invention relates to a process of improving omalizumab biosimilar expression in mammalian cells culture in fed batch mode by maintaining specific temperature 36.5° C.±0.5 throughout cell culture and pH 6.8±0.1 throughout the during the production phase.

In an embodiment, the present process improves the titer about 50% or above, about 60% or above, about 70% or above, about 80% or above, about 90% or above, about 95% or above. and about 98% or above, about 99%, about 100% or above.

Definitions

The term "polypeptide" or "protein" or "antibody of interest" or "glycosylated protein" refers to monoclonal antibody comprised of polypeptide chains, two heavy (H) chains and two light (L) chains inter-connected by disulfide bonds. The mammalian cells being utilized to produce polypeptide by a mammalian cell such as chinese hamster ovary cell are directly secreted polypeptide into the cell culture.

The term "antibody of interest" or "antibody" used herein is an anti-IgE antibody such as omalizumab or ligelizumab. As used herein, anti-IgE antibody inhibits the binding of IgE to the high-affinity IgE receptor (FcεRI) on the surface of mast cells, basophils, and dendritic cells, resulting in FcεRI down-regulation and inhibition IgE-mediated inflammation. These anti-IgE antibodies are useful in the treatment of severe asthma, chronic spontaneous urticaria, nasal polyps etc.

Omalizumab is a recombinant DNA-derived humanized IgG1K monoclonal antibody that selectively binds to human immunoglobulin (IgE). The antibody has a molecular weight of approximately 149 kD. Omalizumab inhibits the interaction of IgE with high affinity IgE receptor (FceRI).

Ligelizumab is a humanized monoclonal antibody with higher affinity binding to human immunoglobulin E (IgE). Ligelizumab inhibits the interaction of IgE with both the high and low affinity IgE receptors (FceRI and FceRII).

The term "biosimilar" or "reference product" or used herein refers to a biologic drug that is highly similar in structure with no clinically meaningful differences in terms of safety, purity, and potency (safety and effectiveness) to a reference product that is already approved by regulatory body against which a proposed biosimilar product is compared.

The term "about", as used herein, is intended to refer to ranges of approximately 10% greater than or less than the referenced value. In certain circumstances, one of skill in the art will recognize that, due to the nature of the referenced value, the term "about" can mean more or less than a 10% deviation from that value.

The term "acidic variants" or "charge variants" or "acidic charge variants" or "percentage of acidic charge variants" used herein refers to acidic species produced during the production process are defined as the antibody variants that elute earlier than the main peak during CEX or later than the main peak during AEX analysis. Sialic acid has been commonly reported to contribute to the formation of acidic species. These charge variants substantially affect the in vitro and in vivo properties of antibodies.

In an embodiment, the percentage of acidic charge variants in an antibody is decreased in comparison to the process where the temperature condition is not maintained 36.5° C.±0.5 and pH 6.8±0.1.

In an embodiment, the percentage of acidic charge variants reduction in anti-IgE antibody refers to the decrease or reduction of acidic charge variants (%) by the process when maintained at 36.5° C.±0.5 temperature during the cell culture and at least pH 6.8 or pH6.9 during the production phase compared with process maintained at 37.5° C. temperature during the cell culture and pH 6.7 during the production phase. The percentage of reduction of acidic charge variants in the anti-IgE antibody selected from about 50%, about 45%, about 40%, about 35%, about 34%, about 33%, about 32%, about 31%, about 30%, about 29%, about 28%, about 27%, about 26%, about 25%, about 20%, about 19%, about 18%, about 17%, about 16%, about 15%, about 14%, about 13%, about 12%, about 11%, about 10%, about 9%, about 8%, about 7%, about 6%, and about 5%.

In an embodiment, the anti-IgE antibody harvested from suitable reactor or bioreactor comprising mammalian cell culture carried out in the process maintained at 36.5° C.±0.5 during the cell culture and at least pH 6.8±0.1 during the production phase comprises the percentage of acidic charge variants selected from about 20% or less, about 19% or less, about 18% or less, about 17% or less, about 16% or less, about 15% or less, about 14% or less, about 13% or less, about 12% or less, about 10% or less, about 9% or less, about 8% or less, about 7% or less, about 6% or less, about 5% or less, about 4% or less.

The term "galactosylation" or "percentage galactosylation of N-glycosylation" or "N-glycosylation percentage (%) of galactosylation" or "Total galactosylation percentage (%)" used herein refers to galactose a unit for the glycosylation chain reaction by linking it next to a N-acetylglucosamine sugar via galactosyltransferase. Galactosylation is known to affect the process of complement dependent (CDC), as the highest modes of action (MOA) of monoclonal antibodies. Furthermore, the low amount of terminal galactosylation required to increase serum half-life of antibody as described in art (Hodoniczky et al., 2005; Miklos et al., 2022).

In an embodiment, the percentage of total galactosylation is decreased in the antibody in comparison to the cell culture process wherein the temperature condition is not maintained 36.5° C.±0.5 during the cell culture and pH 6.8±0.1 during the production phase.

In an embodiment, the total galactosylation percentage (%) reduction in anti-IgE antibody as used herein refers to the decrease or reduction of total galactosylation % by the process when maintained at 36.5° C.±0.5 temperature during the cell culture and at least pH 6.8±0.1 during the production phase compared with cell culture process maintained at 37.5° C. temperature during the cell culture and pH 6.7 during the production phase. The percentage of reduction in total galactosylation of the anti-IgE antibody selected from about 50%, about 49%, about 48%, about 47%, about 46%, about 45%, about 44%, about 43%, about 42%, about 41%, about 40%, about 35%, about 34%, about 33%, about 32%, about 31% about 30%, about 25%, about 20%, about 19%, about 18%, about 17%, about 16%, about 15%, about 14%, about 13%, about 12%, about 11%, about 10%, about 9%, about 8%, about 7%, about 6%, about 5%, about 4%, about 3%, and about 2%.

In an embodiment, the anti-IgE antibody harvested from suitable reactor or bioreactor comprising mammalian cell culture carried out in the process maintained at 36.5° C.±0.5 during the cell culture and at least pH 6.8±0.1 during the production phase comprises total galactosylation percentage selected from about 20% or less, about 19% or less, about 18% or less, about 17% or less, about 16% or less, about 15% or less, about 14% or less, about 13% or less, about 12% or less, about 11% or less, about 10% or less, about 9% or less, about 8% or less, about 7% or less, about 6% or less, about 5% or less, about 4% or less, about 3% or less, about 2% or less, about 1% or less.

The term "bioreactor" used herein, refers to a vessel for culturing or growing cells in nutritive media that supports towards a biologically active environment for culturing of cells, equipped with impeller, spargers etc. The environmental conditions inside the bioreactor, such as temperature, nutrient concentrations, pH, and dissolved gases affect the growth and productivity of the organisms monitored, adjusted, and controlled. The cultures can be grown in shake flasks, small scale bioreactors, and/or large-scale bioreactors. The temperature of the cell culture is maintained by a cooling jacket, coils, or both. The pH of the cell culture is measured and adjusted with small amounts of acid or base, depending upon the biological reaction.

The term "cell culture" or "culture medium" or "production phase" as used herein, refer to culturing of mammalian cells (such as CHO DUKX-B11, CHO S, CHO K1, CHO DG44) capable to product in antibody in bioreactor or fermenter wherein bioreactor comprising a solution or media containing nutrients for growth, propagation, expansion and maintenance of the cells. The cell culture in general comprises the growth and production phase and culturing of cells in culture starts from Day 0, Day 1, Day 2, Day 3, Day 4, Day 6, Day 7, Day 8, Day 9, Day 10, Day 11 or harvest day. Harvest day can be decided by any skilled person when he wishes to terminate the cell culture process in order to recover the product from the Bioreactor. In Fed-batch, cell culture process may last for few days for an example Day 0 to Day 12. Day 0 to Day 2 is considered as growth phase and Day 3 to Day 12 is considered as production phase. However, the duration of growth phase and production phase can be modulated by increasing or decreasing by any skilled person based on his interest in titer, suitable characteristics of products. The term "production phase" used herein starts upon either changing of osmolality or temperature or pH. In the present invention, pH shift if performed on day 3 but the present invention should not be considered limited with pH shifting on Day 3 as any skilled person can envisage the lowering the pH before or after Day 3 as well. It may depend on the duration of process if bioreactor cycle is short for an example 10 days any skilled person may shift the pH before Day 3 in contrast if bioreactor cycle is longer for an example more than 12 days skilled person may shift the pH after Day 3.

In certain embodiment the feeding is performed every day or at suitable interval post at least day 2 onwards. Feeding strategy can be optimized by any skilled person based on the requirement of production, he can feed at any day selected from Day 3 or Day 4, Day 5, Day 6, Day 7, Day 8, Day 9, Day 10, Day 11. Feed media are well known and commercially available and any skilled person can utilize based on his discretion and interest.

The term "temperature" or "suitable temperature" used herein is the temperature set point 36.5° C.±0.5 maintained throughout the system for culturing mammalian cell in a bioreactor. To avoid any doubt, set point is well controlled and does not increase to 37° C. in the present invention and remain to 36° C. to 36.5° C.

The term "suitable pH" used herein is the pH set point 6.8±0.1 maintained from Day 2 or Day 3 onwards throughout the production phase for culturing mammalian cell in a bioreactor.

The present invention provides a production phase where pH is maintained at set point of pH 6.8 and temperature at set point of 36.5° C.

The term "viable cell density" or "VCD" as used herein, refers to the number of live cells present in a given volume of cell culture.

The term "titer" as used herein, refers to the total amount of protein produced by a cell culture in given amount of cell culture volume.

The term "cell viability" as used herein, refers to the percentage of total number of living cells in the cell culture.

The terms "fed batch cell culture" and "fed batch culture," as used herein, refer to a cell culture wherein the cells, preferably mammalian (chinese hamster ovary), and culture media are supplied to the culturing vessel initially and additional culture nutrients are fed, continuously or in discrete increments, to the culture during culturing, with or without periodic cell and/or product harvest before termination of culture. A "fed batch method," refers to a method by which a fed batch cell culture is supplied with additional nutrients. A fed batch method may comprise adding supplemental media as per determined feeding schedule.

In an embodiment, a process for improving the expression of anti-IgE antibody in mammalian cell culture comprising;

a) culturing the mammalian cell capable to express an anti-IgE antibody in the mammalian cell culture;

b) maintaining suitable temperature at 36.5° C.±0.5° C. throughout the mammalian cell culture;

c) harvesting the anti-IgE antibody from mammalian cell culture;

wherein the process improves the titer and has at least 50% high titer and the characteristics of anti-IgE antibody selected from reduced galactosylation and reduced acidic variants.

In an embodiment, a process for improving the expression of an anti-IgE antibody in mammalian cell culture comprising;

a) culturing the mammalian cells capable to express an anti-IgE antibody in the mammalian cell culture;

b) maintaining suitable temperature at 36.5° C.±0.5 throughout the mammalian cell culture;

c) harvesting the anti-IgE antibody from mammalian cell culture;

wherein the process improves the titer and characteristics of anti-IgE antibody selected from reduced galactosylation and reduced acidic variants.

In an embodiment, the suitable temperature is 36.5±0.5° C.

In an embodiment, a process for improving the expression of an anti-IgE antibody in mammalian cell culture comprising;

a) culturing the mammalian cells capable to express an anti-IgE antibody in the mammalian cell culture;

b) maintaining suitable temperature at 36.5° C.±0.5 throughout the mammalian cell culture;

c) harvesting the anti-IgE antibody from mammalian cell culture;

wherein the process improves the titer and characteristics of anti-IgE antibody selected from reduced galactosylation and reduced acidic variants.

In an embodiment, the suitable temperature is 36.5° C.±0.5.

In an embodiment, a process for improving the expression of omalizumab in mammalian cell culture comprising;

a) culturing the mammalian cell capable to express omalizumab in the mammalian cell culture;

b) maintaining suitable temperature 36.5° C.±0.5 throughout the mammalian cell culture;

c) maintaining about pH 6.8±0.1 during the production phase of mammalian cell culture;

d) harvesting omalizumab from mammalian cell culture;

wherein the process improves the titer and characteristics of omalizumab selected from reduced galactosylation and reduced acidic variants.

In an embodiment, the suitable pH less than 7.

In an embodiment, the suitable pH selected from about pH 6.7, about pH 6.8, and about 6.9 maintained during the production phase.

In an embodiment, the suitable pH is maintained during the production phase on day selected from Day 3, Day 4, Day 5, Day 6, Day 7, Day 8, Day 9, Day 10, Day 11, and Day 12.

In an embodiment, a process for the production of antibody comprising:

a) culturing the mammalian cell capable to express antibody of interest in the bioreactor;

b) maintaining the suitable temperature 36.5° C. throughout the cell culture and at least pH about 6.8 during the production phase in the bioreactor;

c) harvesting the antibody of interest from mammalian cell culture;
  wherein the antibody of interest has at least 50% high titer compared to the mammalian cell is cultured during production phase at above 36.5° C. and pH less than 6.8.

In an embodiment, a process for the production of antibody comprising:
  a) culturing the mammalian cells capable to express antibody of interest in the bioreactor;
  b) maintaining the suitable temperature 36.5° C. throughout the cell culture and at least pH about 6.8 during the production phase in the bioreactor;
  c) harvesting the antibody of interest from mammalian cell culture in the bioreactor;
    wherein the antibody of interest has reduced galactosylation compared to the mammalian cell is cultured during production phase at above 36.5° C. and pH less than 6.8.

In an embodiment, a process for the production of omalizumab comprising:
  a) culturing the mammalian cell capable to express omalizumab in the bioreactor;
  b) maintaining the suitable temperature 36.5° C. throughout the cell culture and at least pH about 6.8 during the production phase in the bioreactor;
  c) harvesting omalizumab from mammalian cell culture contains at least 50% high titer and reduced galactosylation and/or reduced acidic variants compared to the mammalian cell is cultured during production phase at above 36.5° C. and pH less than 6.8.

In an embodiment, a process for the production of antibody comprising:
  a) culturing the mammalian cell capable to express antibody of interest in the bioreactor;
  b) maintaining the mammalian cell at one suitable temperature set point and at first pH in the bioreactor;
  c) maintaining the mammalian cell at one suitable temperature set point and at second pH in the bioreactor wherein the second pH is at least one log lower than first pH;
  d) harvesting the antibody of interest from bioreactor comprising mammalian cell culture;
    wherein the antibody of interest has reduced galactosylation and/or reduced acidic variants.

In certain embodiment the pH is maintained below 7 during production phase. In certain embodiment the cell culture process is initiated at or above pH7 preferably pH 7.1 or pH7.2 and reduced to pH below 7 preferably pH 6.7 to 6.9.

In certain embodiment, the second pH is lower than first pH by unit selected from one log, two log, three log.

In certain embodiment, the first pH is selected from pH 6.8, 6.9, 7.0,

In certain embodiment, the first pH is maintained for suitable period selected from Day 0, Day 1, Day 2 and Day 3.

In certain embodiment, the second pH is selected from pH 6.5, 6.6, 6.7 6.8, 6.9, 7.0, 7.1 and 7.2.

In certain embodiment, the second pH is maintained for suitable period selected from Day 4, Day 5, Day 6 and Day 7, Day 8, Day 9, Day 10, Day 11 and Day 12.

In an embodiment, the mammalian cells in cell culture are Chinese hamster ovary (CHO) cells.

In an embodiment, the temperature ranging for culturing of cells selected from about 36° C. to about 36.5° C.

In certain embodiment, the temperature for cell culturing is 36.5° C.±0.5.

In an embodiment, the pH of cell culturing from about pH 6 to about pH 7.5.

In certain embodiment, the pH of cell culturing is about pH 6.8±0.1.

In an embodiment, the dissolve oxygen (DO) rate in bioreactor is selected from 10%, 20%, 30%, 40%, 50%, 60%. In certain embodiment, the DO rate in bioreactor is 40%.

In an embodiment, the percentage of total galactosylation in an antibody is decreased in comparison to the process where the temperature condition is not maintained 36.5° C.±0.5 and pH 6.8±0.1.

In an embodiment, the reduction of total galactosylation in the anti-IgE antibody selected from about 50%, about 49%, about 48%, about 47%, about 46%, about 45%, about 44%, about 43%, about 42%, about 41%, about 40%, about 35%, about 34%, about 33%, about 32%, about 31% about 30%, about 25%, about 20%, about 19%, about 18%, about 17%, about 16%, about 15%, about 14%, about 13%, about 12%, about 11%, about 10%, about 9%, about 8%, about 7%, about 6%, about 5%, about 4%, about 3%, and about 2%.

In an embodiment, the anti-IgE antibody comprises total galactosylation percentage selected from about 20% or less, about 19% or less, about 18% or less, about 17% or less, about 16% or less, about 15% or less, about 14% or less, about 13% or less, about 12% or less, about 10% or less, about 9% or less, about 8% or less, about 7% or less, about 6% or less, about 5% or less, about 4% or less, about 3% or less, about 2% or less, about 1% or less.

In certain embodiment, the anti-IgE antibody comprises total galactosylation percentage about 12% or less, about 10% or less, about 9% or less, about 8% or less.

In an embodiment, the anti-IgE antibody comprises percentage of total galactosylation about 12% or less.

In an embodiment, the anti-IgE antibody comprises total galactosylation percentage about 10% or less.

In an embodiment, the anti-IgE antibody comprises total galactosylation percentage about 9% or less.

In an embodiment, the anti-IgE antibody comprises total galactosylation percentage about 8% or less.

In an embodiment, the percentage of acidic charge variants in an antibody is decreased in comparison to the process where the temperature condition is not maintained 36.5° C.±0.5 and pH 6.8±0.1.

In an embodiment, the reduction of acidic charge variants in the anti-IgE antibody selected from about 50%, about 45%, about 40%, about 35%, about 34%, about 33%, about 32%, about 31%, about 30%, about 29%, about 28%, about 27%, about 26%, about 25%, about 20%, about 19%, about 18%, about 17%, about 16%, about 15%, about 14%, about 13%, about 12%, about 11%, about 10%, about 9%, about 8%, about 7%, about 6%, and about 5%.

In an embodiment, the anti-IgE antibody comprises percentage of acidic charge variants selected from about 20% or less, about 19% or less, about 18% or less, about 17% or less, about 16% or less, about 15% or less, about 14% or less, about 13% or less, about 12% or less, about 10% or less, about 9% or less, about 8% or less, about 7% or less, about 6% or less, about 5% or less, and about 4% or less.

In certain embodiment, the anti-IgE antibody comprises percentage of acidic charge selected from about 16% or less, about 15% or less, about 12% or less.

In an embodiment, the antibody of interest comprises total galactosylation percentage about 16% or less.

In an embodiment, the antibody of interest comprises total galactosylation percentage about 15% or less.

In an embodiment, the antibody of interest comprises percentage of acidic charge variants about 12% or less.

In an embodiment, the process increases the titer of anti-IgE antibody about 50% or above, about 60% or above, about 64% or above, about 70% or above, about 80% or above, about 90% or above, about 95% or above, about 98% or above, about 99% or above, about 100% or above, about 101% or above, about 102% or above, about 103% or above, about 104% or above, about 105% or above, about 106% or above, about 110% or above, about 115% or above, about 120% or above, about 125% or above, about 126% or above, about 127% or above, about 128% or above, about 129% or above, about 130% or above, about 135% or above, about 136% or above, about 137% or above, about 138% or above, about 140% or above, about 150% or above, about 151% or above, about 152% or above, about 155% or above, about 160% or above, about 161% or above, about 162% or above, about 163% or above, about 164% or above, about 165% or above, about 170% or above, about 180% or above, about 190% or above.

In certain embodiment, the process increases the titer of anti-IgE antibody about 64% or above.

In certain embodiment, the process increases the titer of anti-IgE antibody about 105% or above.

In certain embodiment, the process increases the titer of anti-IgE antibody about 128% or above.

In certain embodiment, the process increases the titer of anti-IgE antibody about 135% or above.

In certain embodiment, the process increases the titer of anti-IgE antibody about 150% or above.

In certain embodiment, the process increases the titer of anti-IgE antibody about 160% or above.

In an embodiment, an antibody of interest product shows percentage identity profile to the reference product selected from at least 80%, at least 85%, at least 90%, at least 95%, at least 100%.

In an embodiment, the viable cell density at day 12 is selected from >15×10^6 cell/mL or above, 20×10^6 cell/mL or above, 25×10^6 cell/mL or above, 30×10^6 cell/mL or above, 35×10^6 cell/mL or above, >40×10^6 cell/mL or above, >50×10^6 cell/mL or above.

In certain embodiment, the viable cell density at day 12 is about >30×10^6 cell/mL or above.

In an embodiment, the viability of cells at day 12 is selected from about 50% or above, about 60% or above, 70% or above, 80% or above.

In certain embodiment, the viability of cells at day 12 is 50% or above.

In an embodiment, the process is performed in a fed batch mode, or continuous mode or perfusion mode.

In preferred embodiment, an antibody of interest is omalizumab or ligelizumab.

In an embodiment, a process for improving the expression of omalizumab in mammalian cell culture comprising;
   a) culturing the mammalian cell capable to express omalizumab in the mammalian cell culture;
   b) maintaining temperature 36.5±0.5° C. throughout the mammalian cell culture;
   c) maintaining about pH 6.8±0.1 during the production phase of mammalian cell culture;
   d) harvesting omalizumab from mammalian cell culture;
      wherein the process improves the titer more than 50% and characteristics of omalizumab selected from reduced galactosylation and reduced acidic variants.

In an embodiment, a process for improving the expression of omalizumab in mammalian cell culture comprising;
   a) culturing the mammalian cell capable to express omalizumab in the mammalian cell culture;
   b) maintaining temperature 36.5±0.5° C. throughout the mammalian cell culture;
   c) maintaining about pH 6.8±0.1 during the production phase of mammalian cell culture;
   d) harvesting omalizumab from mammalian cell culture;
      wherein the process improves the titer more than 50% and characteristics of omalizumab selected from total galactosylation about 12% or less and acidic variants about 16% or less.

Example 1

The monoclonal antibody cell bank vial was thawed Shake flask 125 (SF125) into the seed media and cell counts were checked. The incubation was continued for 3-4 days during which cells reach the optimum cell density for subculture. cells were subsequently expanded to Shake flask 250 (SF250) and Shake flask 500 (SF500) to generate sufficient inoculum for 5 L glass bioreactors (working volume 3500 mL). Production Fed batch bioreactor run was executed at 5 L glass bioreactor using process parameters as mentioned below. The overall batch cycle was for 12 days and was harvested depending upon the culture viability.

| Control Process | | | |
|---|---|---|---|
| Sr. No | Process Parameter | Unit | Setpoints/parameter details |
| 1 | Post Inoculation Initial volume | mL | 3500 |
| 2 | DO % | % Saturation | 40 |
| 3 | pH | N/A | 7.1 ± 0.3 day 0-2, 6.7 ± 0.1 day 3-harvest |
| 4 | Temperature | ° C. | 37.5 |
| 5 | Agitation rate | RPM | 250 |
| 6 | Initial seeding cell density | ×10^6 cells/mL | 0.5 |
| 7 | Feed medium | % v/v | 3.3% (Day 3-11) |
| 8 | Sodium bicarbonate | mL | As per requirement for pH maintenance (Auto mode) |
| 9 | Antifoam | % | Up to 10% addition (as required) |
| 10 | % DO maintenance by | mL/min | Air + O2 |
| 11 | Air flow. | mL/min | 0-200 |
| 12 | O$_2$ flow | mL/min | 0-500 |

-continued

| | Control Process | | |
|---|---|---|---|
| Sr. No | Process Parameter | Unit | Setpoints/parameter details |
| 13 | Air overlay flow rate | mL/min | 0-100 |
| 14 | Harvest Criteria | N/A | Day 12 or Viability ≤ 70% which comes first |

| | Temperature 36.5-degree Process | | |
|---|---|---|---|
| Sr. No | Process Parameter | Unit | Setpoints/parameter details |
| 1-14 | All parameters as per Control Process except below parameters | | |
| 15 | Temperature | ° C. | 36.5 |
| 16 | pH | N/A | 7.1 ± 0.3 day 0-2, 6.8 ± 0.1 day 3-harvest |

The process with 36.5-degree temperature and pH set point of 7.1±0.3 day 0-2, 6.8±0.1 day 3-harvest along with control process in 5 L bioreactor fed batch run was conducted. Harvest was performed in both the batches by centrifugation of cells at followed by 0.2 μm filtration. NPEL generated from day 12 harvests and samples were analysed for titer by protein A HPLC, % Acidic charge variants by CEX-HPLC method and N-Glycosylation (% Total galactosylation) check by HILIC-UPLC method. Following observations were made pertaining to Titer and product quality as below.

a) Titer was increased by 135.6% (Batch 1), 128.2% (Batch 2), 162.8% (Batch 3).

b) Total % Galactosylation was decreased by 16.1% (Batch 1), 31.8% (Batch 2), 15.7% (Batch 3).

c) % Acidic charge variants were decreased by 29.1% (Batch 1), 30.6% (Batch 2), 28.8% (Batch 3).

| Parameters | Control Process with 37.5 degree and pH 6.7 | Process with 36.5 degree and pH 6.8 ± 0.1 (Batch 1) | Process with 36.5 degree and pH 6.8 ± 0.1 (Batch 2) | Process with 36.5 degree and pH 6.8 ± 0.1 (Batch 3) |
|---|---|---|---|---|
| Titer (g/L) | 1.91 | 4.50 | 4.36 | 5.02 |
| Total Galactosylation (%) by N-Glycan Analysis | 15.15 | 12.7 | 10.32 | 12.76 |
| % Acidic charge variants (%) | 17.51 | 12.4 | 12.14 | 12.45 |

Example 2

The monoclonal antibody cell bank vial is thawed Shake flask 125 (SF125) into the seed media and cell counts are checked. The incubation is continued for 3-4 days during which cells reach the optimum cell density for subculture cells are subsequently expanded to Shake flask 250 (SF250) and Shake flask 500 (SF500) to generate sufficient inoculum for 5 L glass bioreactors (working volume 3500 mL). Production Fed batch bioreactor run is executed at 5 L glass bioreactor using process parameters as mentioned below. The overall batch cycle is for 12 days and harvested depending upon the culture viability.

| Sr. No | Process Parameter | Unit | Setpoints/parameter details |
|---|---|---|---|
| 1 | Post Inoculation Initial volume | mL | 3500 |
| 2 | DO % | % Saturation | 40 |
| 3 | pH | N/A | 7.1 ± 0.3 day 0-2, 6.8 day 3-harvest |
| 4 | Temperature | ° C. | 35.5 |
| 5 | Agitation rate | RPM | 250 |
| 6 | Initial seeding cell density | ×10$^6$ cells/mL | 0.5 |
| 7 | Feed medium | % v/v | 3.3% (Day 3-11) |
| 8 | Sodium bicarbonate | mL | As per requirement for pH maintenance (Auto mode) |
| 9 | Antifoam | % | Up to 10% addition (as required) |
| 10 | % DO maintenance by | mL/min | Air + O2 |
| 11 | Air flow. | mL/min | 0-200 |
| 12 | O$_2$ flow | mL/min | 0-500 |

-continued

| Sr. No | Process Parameter | Unit | Setpoints/parameter details |
|---|---|---|---|
| 13 | Air overlay flow rate | mL/min | 0-100 |
| 14 | Harvest Criteria | N/A | Day 12 or Viability ≤ 70% which comes first |

The process with 35.5-degree temperature and pH set point of 7.1±0.3 day 0-2, 6.8 day 3-day 12 (harvest) the process in 5 L bioreactor fed batch run is conducted. Harvest bioreactor using process parameters as mentioned below. The overall batch cycle was for 12 days and was harvested depending upon the culture viability.

| Sr. No | Process Parameter | Unit | Setpoints/parameter details |
|---|---|---|---|
| 1 | Post Inoculation Initial volume | L | 185 |
| 2 | DO % | % Saturation | 40% |
| 3 | pH | N/A | 7.1 ± 0.3 Day 0-2<br>6.8 ± 0.1 Day 3-12 |
| 4 | Temperature | ° C. | 36.5° C. ± 0.5° C. |
| 5 | Agitation rate | RPM | 108 |
| 6 | Initial seeding cell density | $\times 10^6$ cells/mL | 0.5 |
| 7 | Feed medium | % v/v | Feed 3.3%<br>Days 3 to 11 inclusive |
| 8 | Sodium bicarbonate | mL | As per requirement for pH maintenance (Auto mode) |
| 9 | Antifoam | % | Up to 10% addition (as required) |
| 10 | % DO maintenance by | L/min | Air + O2 |
| 11 | Air flow. | L/min | 3.2 lpm |
| 12 | O2 flow | L/min | On demand (cascade) |
| 13 | Air overlay flow rate | L/min | 1.0 lpm |
| 14 | Harvest Criteria | N/A | Day 12 or within 24 hours when the cell culture viability is <70% | is performed by centrifugation of cells at followed by 0.2 μm filtration. NPEL generated from day 12 harvest and samples are analysed for Titer by protein A HPLC, % Acidic charge variants by CEX-HPLC method and N-Glycosylation (% Total galactosylation) check by HILIC-UPLC method. Following observations are made pertaining to Titer and product quality shown below when compared with 36.5 degree and pH 6.8±0.1.

a) Titer was increased by 64.23.%.

b) Total % Galactosylation was decreased by 2.38%.

| Parameter | Process with 35.5 degree and pH 6.8 | Process with 36.5 degree and pH 6.8 ± 0.1 |
|---|---|---|
| Titer (g/L) | 2.74 | 4.50 |
| Total Galactosylation (%) by N-Glycan Analysis | 13.01 | 12.7 |

Example 3

The monoclonal antibody cell bank vial was thawed Shake flask 125 (SF125) into the seed media and cell counts were checked. The incubation was continued for 3-4 days during which cells reach the optimum cell density for subculture. cells were subsequently expanded to Shake flask 500 (SF500) and Shake flask 3000 (SF3000) to 50 L seed bioreactor to generate sufficient inoculum 5 for 200 L single use bioreactors (working volume 185 L). Production Fed batch bioreactor run was executed at 200 L single use The process with 36.5-degree temperature and pH set point of 7.1±0.3 day 0-2, 6.8±0.1 day 3-harvest in 200 L bioreactor fed batch run was conducted. Harvest was performed by two-stage depth filtration followed by 0.2 μm filtration. NPEL generated from Day 12 harvest and sample ware analyzed for Titer by protein A HPLC, % Acidic charge variants by CEX-HPLC method and N-Glycosylation (% Total galactosylation) check by HILIC-UPLC method. Following observations were made pertaining to Titer and product quality shown below when compared with control process results at 37.5 degree and pH 6.7.

a) Titer was increased by 105.75%.

b) Total Galactosylation was decreased by 41.98%.

c) % Acidic charge variants were decreased by 11.9%.

| Parameters | Scale 200 L |
|---|---|
| Day 12 Titer (mg/mL) | 3.93 |
| Day 12 Total Galactosylated (%) by N-Glycan Analysis | 8.79 |
| Day 12 Acidic charge variants (%) | 15.41 |

Example 4

The monoclonal antibody cell bank vial was thawed Shake flask 125 (SF125) into the seed media and cell counts were checked. The incubation was continued for 3-4 days during which cells reach the optimum cell density for subculture. cells were subsequently expanded to Shake flask 500 (SF500) and Shake flask 3000 (SF3000) and 50 L seed bioreactor to generate sufficient inoculum for 500 L single use bioreactors (working volume 350 L). Production Fed batch bioreactor run was executed at 500 L single use bioreactor using process parameters as mentioned below. The overall batch cycle was for 12 days and was harvested depending upon the culture viability.

| S. No | Process Parameter | Set-point/parameter details |
|---|---|---|
| 1 | Post Inoculation Initial volume (L) | 360 L |
| 2 | Initial VCD ($\times 10^6$ cells/mL) | 0.50 |
| 3 | Temperature (° C.) | 36.5° C. ± 0.5° C. |
| 4 | pH (Day 0-Day 2) | 7.1/ dead band 0.3 |
| 5 | pH (Day 2-Day 3) | 7.0/ dead band 0.3 |
| 6 | pH (Day 3-Harvest) | 6.8 / dead band 0.1 |
| 7 | Dissolved Oxygen % (% Saturation) | 40 |
| 8 | Agitation speed (RPM) | 74 |
| 9 | Overlay Air (L/min) | 3.0 |
| 10 | Air flow rate (L/min) | Day 0-3.0, Day 1-6.0, Day 2-9.0, Day 3-12.0 |
| 11 | Oxygen flow rate (L/min) | On demand (cascade) |
| 12 | $CO_2$ flow rate (L/min) | On demand (cascade) |
| 13 | Antifoam Strategy (%) | Add 10% antifoam "as needed basis" |
| 14 | Feeding Strategy (% v/v) | 3.3% Days 3 to 11 |
| 15 | Sodium Bicarbonate (mL) | 7.5% Sodium Bicarbonate As per need to maintain pH set point |
| 16 | Harvest Criteria | Day 12 or within 24 hours when the cell culture viability is <70% |

The process with 36.5-degree temperature and pH set point of 7.1±0.3 day 0-2, 7.0±0.3 day 2-3, 6.8±0.1 day 3-harvest in 500 L bioreactor fed batch run was conducted. Harvest was performed by two-stage depth filtration followed by 0.2 µm filtration. NPEL generated from Day 12 harvest and sample ware analyzed for Titer by protein A HPLC, % Acidic charge variants by CEX-HPLC method and N-Glycosylation (% Total galactosylation) check by HILIC-UPLC method. Following observations were made pertaining to Titer and product quality shown below when compared with control process results at 37.5 degree and pH 6.7.

a) Titer was increased by 150.75%.

b) Total % Galactosylation was decreased by 40.59%.

c) % Acidic charge variants were decreased by 6.91%.

| Parameters | Scale 500 L |
|---|---|
| Day 12 Titer (mg/mL) | 4.79 |
| Day 12 Total Galactosylated (%) by N-Glycan Analysis | 9 |
| Day 12 Acidic Variants (%) | 16.30 |

The invention claimed is:

1. A process for improving the expression of omalizumab in Chinese Hamster Ovary cell culture comprising;

a) culturing the Chinese Hamster Ovary cells capable to express omalizumab in the Chinese Hamster Ovary cell culture;

b) maintaining suitable temperature at 36.5° C. throughout the Chinese Hamster Ovary cell culture;

c) harvesting the omalizumab from the Chinese Hamster Ovary cell culture, wherein the process improves titer of the omalizumab compared to cell culture process performed at temperature 35.5° C. or 37.5° C., and wherein the process reduces total galactosylation of the omalizumab or reduces expression of acidic variants of the omalizumab compared to cell culture process performed at temperature 35.5° C. or 37.5° C.

2. The process as claimed in claim 1, wherein the Chinese Hamster Ovary culture comprises a growth phase and a production phase, wherein the production phase maintains suitable pH selected from pH 6.7, pH 6.8, and pH 6.9.

3. The process as claimed in claim 1, wherein the process increases the titer of the omalizumab by 50%±5% to 190±19% compared to cell culture process performed at temperature 35.5° C. or 37.5° C.

4. The process as claimed in claim 1, wherein the process reduces total galactosylation of the omalizumab 2%±0.2% to 50%±5% compared to cell culture process performed at temperature 35.5° C. or 37.5° C.

5. The process as claimed in claim 1, wherein the process results in total galactosylation of the omalizumab of less than 13%.

6. The process as claimed in claim 1, wherein the process results in total galactosylation of the omalizumab of 8%±0.8% to 12%±1.2%.

7. The process as claimed in claim 1, wherein the process reduces expression of acidic variants of the omalizumab 5%±0.5% to 50%±5% compared to cell culture process performed at temperature 35.5° C. or 37.5° C.

8. The process as claimed in claim 1, wherein the process results in expression of acidic variants of the omalizumab of less than 17%.

9. The process as claimed in claim 1, wherein the process results in expression of acidic variants of the omalizumab of 12%±1.2% to 16%±1.6% compared to cell culture process performed at temperature 35.5° C. or 37.5° C.

10. A process for improving the expression of omalizumab in Chinese Hamster Ovary cell culture comprising:

a) culturing the Chinese Hamster Ovary cells capable to express omalizumab in the Chinese Hamster Ovary cell culture;

b) maintaining temperature 36.5° C. throughout the Chinese Hamster Ovary cell culture;

c) maintaining pH 6.8±0.1 during the production phase of mammalian cell culture;

d) harvesting omalizumab from Chinese Hamster Ovary cell culture, wherein the process improves titer of the omalizumab compared to cell culture process performed at temperature 35.5° C. or 37.5° C., and wherein the process results in total galactosylation of the omalizumab of 8%±0.8% to 12%±1.2% compared to cell culture process performed at temperature 35.5° C. or 37.5° C. or wherein the process results in expression of acidic variants of the omalizumab of 12%±1.2% to 16%±1.6% compared to cell culture process performed at temperature 35.5° C. or 37.5° C.

11. The process as claimed in claim 10, wherein the process is performed in a fed batch mode, or continuous mode or perfusion mode.

12. The process as claimed in claim 1, wherein the process is performed in a fed batch mode, or continuous mode or perfusion mode.

\* \* \* \* \*